(12) United States Patent
Zhang et al.

(10) Patent No.: US 7,776,580 B2
(45) Date of Patent: Aug. 17, 2010

(54) MAGNETISM BASED RAPID CELL SEPARATION

(75) Inventors: Xu Zhang, Beijing (CN); Xin Xie, Beijing (CN); Depu Chen, Beijing (CN); Weiyang Fei, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 10/538,498

(22) PCT Filed: Dec. 31, 2002

(86) PCT No.: PCT/CN02/00942

§ 371 (c)(1), (2), (4) Date: Jan. 9, 2006

(87) PCT Pub. No.: WO2004/053115

PCT Pub. Date: Jun. 24, 2004

(65) Prior Publication Data

US 2006/0141450 A1  Jun. 29, 2006

(30) Foreign Application Priority Data

Dec. 9, 2002  (CN) ................................ 02 1 53992

(51) Int. Cl.
*C12N 7/02* (2006.01)
*C12N 5/00* (2006.01)
*C12N 1/02* (2006.01)
*C12P 19/34* (2006.01)
*G01N 33/50* (2006.01)

(52) U.S. Cl. ....................... 435/239; 435/325; 435/261; 435/91.1

(58) Field of Classification Search ..................... None
See application file for complete search history.

(56) References Cited

U.S. PATENT DOCUMENTS

| | | |
|---|---|---|
| 4,001,197 A | 1/1977 | Mitchell et al. |
| 4,230,685 A | 10/1980 | Senyei et al. |
| 4,336,173 A | 6/1982 | Ugelstad |
| 4,421,660 A | 12/1983 | Solc nee Hajna |
| 4,490,436 A | 12/1984 | Kawakami et al. |

(Continued)

FOREIGN PATENT DOCUMENTS

CN  1175282  3/1998

(Continued)

OTHER PUBLICATIONS

Bidawid, et al. Rapid concentration and detection of hepatitis A virus from lettuce and strawberries. J Virol. Meth. 2000; 88:175-185.*

(Continued)

*Primary Examiner*—Mary E Mosher
*Assistant Examiner*—Stuart W Synder
(74) *Attorney, Agent, or Firm*—Morrison & Foerster LLP (57) ABSTRACT

This invention relates generally to the field of cell seperation. In particular, the invention provides processes for isolating a target cell, cellular organelle or virus from a sample, using inter alia, nonspecific binding between a target cell, cellular organelle or virus with a magnetic microbead modified to comprise hydroxyl, carboxyl or epoxy groups.

38 Claims, 1 Drawing Sheet

U.S. PATENT DOCUMENTS

| | | | |
|---|---|---|---|
| 4,554,088 | A | 11/1985 | Whitehead et al. |
| 4,654,267 | A | 3/1987 | Ugelstad et al. |
| 4,683,195 | A | 7/1987 | Mullis et al. |
| 4,683,202 | A | 7/1987 | Mullis |
| 4,774,265 | A | 9/1988 | Ugelstad et al. |
| 4,965,007 | A | 10/1990 | Yudelson |
| 5,091,206 | A | 2/1992 | Wang et al. |
| 5,232,789 | A | 8/1993 | Platz et al. |
| 5,279,936 | A | 1/1994 | Vorpahl et al. |
| 5,283,079 | A | 2/1994 | Wang et al. |
| 5,318,797 | A | 6/1994 | Matijevic et al. |
| 5,395,688 | A | 3/1995 | Wang et al. |
| 5,409,818 | A | 4/1995 | Davey et al. |
| 5,536,644 | A * | 7/1996 | Ullman et al. ............. 435/7.25 |
| 5,554,517 | A | 9/1996 | Davey et al. |
| 5,691,208 | A | 11/1997 | Miltenyi et al. |
| 5,695,946 | A | 12/1997 | Benjamin et al. |
| 5,834,121 | A | 11/1998 | Sucholeiki et al. |
| 6,908,759 | B2 | 6/2005 | Jang |
| 2002/0009738 | A1 | 1/2002 | Houghton et al. |
| 2002/0058019 | A1* | 5/2002 | Berenson et al. ........... 424/93.7 |

FOREIGN PATENT DOCUMENTS

| | | |
|---|---|---|
| CN | 1355319 | 6/2002 |
| CN | 1375507 | 10/2002 |
| DE | 278 598 | 5/1990 |
| EP | 0 768 530 | 10/1995 |
| EP | 1 108 743 | 6/2001 |
| WO | WO-83/03920 | 11/1983 |
| WO | WO-91/12079 | 8/1991 |
| WO | WO-92/17609 | 10/1992 |
| WO | WO-98/04745 | 2/1998 |
| WO | WO-98/38293 | 9/1998 |
| WO | WO-98/51693 | 11/1998 |
| WO | WO-00/29562 | 5/2000 |
| WO | WO-00/61803 | 10/2000 |
| WO | WO-01/55438 | 8/2001 |
| WO | WO-02/075309 | 9/2002 |

OTHER PUBLICATIONS

Antoinea, et al. Lymphoid cell fractionation on magnetic polyacrylamide-agarose beads. Immunology. 1978; 15(7):443-452.*
Brinchmann, et al. Few Infected CD4+ T Cells but a High Proportion of Replication-Competent Provirus Copies in Asymptomatic Human Immunodeficiency Virus Type I Infection. J Virol. 1991; 65(4):2019-2023.*
Janssen WE, Rios AM. Non-specific cell binding characteristics of para-magnetic polystyrene microspheres used for antibody-mediated cell selection. J Immunol Methods. Jul. 26, 1989;121(2):289-94.*
Fletcher M. The effects of proteins on bacterial attachment to polystyrene. J Gen Microbiol. Jun. 1976;94(2):400-4.*
Kemshead and Ugelstad. Magnetic separation techniques: their application to medicine. Mol.Cell. Biochem. 1985; 67:11-18.*
Rudi, et al. Detection of Toxin-Producing Cyanobacteria by Use of Paramagnetic Beads for Cell Concentration and DNA Purification. Appl Environ Microbiol. 1998; 64(1):34-37.*
Vesper and Bauer. Role of Pili (Fimbriae) in Attachment of *Bradyrhizobium japonicum* to Soybean Roots. Applied and Environmental Microbiology. Jul. 1986; vol. 52, No. 1: p. 134-141.*
Maki, et al. Factors Controlling Attachment of Bryozoan Larvae: A Comparison of Bacterial Films and Unfilmed Surfaces. Biol. Bull. Oct. 1989; 177: 295-302.*
Genevaux, et al. A rapid screening procedure to identify mini-TnlO insertion mutants of *Escherichia coli* K-12 with altered adhesion properties. FEMS Microbiology Letters. 1996; 142:27-30.*
Trafny, EA. Susceptibility of adherent organisms from *Pseudomonas aeruginosa* and *Staphylococcus aureus* strains isolated from burn wounds to antimicrobial agents. International Journal of Antimicrobial Agents. 1998; 10:223-228.*
Pringle and Fletcher. Influence of Substratum Hydration and Adsorbed Macromolecules on Bacterial Attachment to Surfaces. Applied and Environmental Microbiology. 1986; vol. 51, No. 6:1321-1325.*
International Search Report for PCT/CN02/00942, mailed on Jun. 12, 2003, 1 page.
Matijevic, Acc. Chem. Res. (1981) 14:22-29.
Vandenberge et al., J. of Magnetism and Magnetic Materials (1980) 15-18:1117-1118.
Dauer et al., Biotechnology and Bioengineering (1991) 37(11):1021-1028.
Safarik et al., Journal of Chromatography B (1999) 722:33-53.
Supplementary European Search Report for EP 02808210.5, mailed on Sep. 8, 2006, 6 pages.
Xie at al., Journal of Magnetism and Magnetic Materials (2004) 280(2-3):164-168.
Xie at al., Journal of Magnetism and Magnetic Materials (2004) 277(1-2):16-23.
Examiner's report for Australian application No. 2002357423, mailed Apr. 23, 2007, 3 pages.
European Office Action for European application No. 02 808 210.5, mailed Jun. 15, 2007, 8 pages.
Hardingham et al., Cancer Research (1993) 53:3455-3458.
International Search Report for PCT/CN02/00940, mailed on Apr. 10, 2003, 2 pages.
Inuma et al., Int. J. Cancer (2000) 89:337-344.
Lopez-Sabater et al., Letters in Applied Microbiology (1997) 24:101-104.
Olsvik et al., Clinical Microbiology Reviews (1994) 7(1):43-54.
Supplementary European Search Report for EP 02808209.7, mailed on Nov. 10, 2005, 3 pages.
Widjojoatmodjo et al., Journal of Clinical Microbiology (1992) 30(12):3195-3199.
U.S. Appl. No. 10/538,443, filed Jun. 10, 2005.
Preliminary Amendment for U.S. Appl. No. 10/538,443, filed Jun. 10, 2005.
Restriction Requirement for U.S. Appl. No. 10/538,443, mailed on Dec. 13, 2007.
Response to Restriction Requirement for U.S. Appl. No. 10/538,443, filed Jan. 11, 2008.
Non-Final Office Action for U.S. Appl. No. 10/538,443, mailed on Mar. 19, 2008.
Fazeli et al., J Virol Methods (1998) 70:201-211.
Gilpatrick et al., J Virol Methods (2000) 90:69-78.
Notice of Reasons for Rejection for Japanese Patent Application No. 2004-557740, mailed on Mar. 5, 2009, 9 pages.
Grevelding et al., Nucleic Acids Research (1996) 24(20):4100-4101.
Office Action for European Patent Application No. EP 02 808 209.7, mailed on Jun. 12, 2008, 6 pages.
Amendment in Response to Non-Final Office Action for U.S. Appl. No. 10/538,443, filed Jun. 3, 2008, 14 pages.
Final Office Action for U.S. Appl. No. 10/538,443, mailed on Oct. 17, 2008, 16 pages.
Amendment After Final Action for U.S. Appl. No. 10/538,443, filed Dec. 12, 2008, 12 pages.
Advisory Action for U.S. Appl. No. 10/538,443, mailed on Jan. 6, 2009, 3 pages.
First Preliminary Amendment and Request for Continued Examination for U.S. Appl. No. 10/538,344, filed Jan. 8, 2009, 12 pages.
Request for Continued Examination for U.S. Appl. No. 10/538,443, filed Jan. 8, 2009.
Non-Final Office Action for U.S. Appl. No. 10/538,443, mailed on Mar. 18, 2009, 17 pages.
Kondo et al., Journal of Fermentation and Bioengineering (1997) 84(4):337-341.
Notice of Final Rejection for JP 2004-557741, mailed Apr. 20, 2010, 6 pages.

* cited by examiner

MAGNETISM BASED RAPID CELL SEPARATION

CROSS-REFERENCE TO RELATED APPLICATIONS

This application is the national phase of PCT application PCT/CN2002/000942 having an international filing date of Dec. 31, 2002, which claims priority from China application number 02 1 53992.8 filed Dec. 9, 2002. The contents of these documents are incorporated herein by reference.

TECHNICAL FIELD

This invention relates generally to the field of cell, cellular organelle or virus isolation. In particular, the invention provides processes and kits for isolating a target cell, cellular organelle or virus from a sample, using inter alia, non- or low-specific binding between a target cell, cellular organelle or virus with a magnetic microbead.

BACKGROUND ART

The development level of biology depends on the gentle and effective preparation of biological samples. It is often the rate-limiting step to separate the biological materials, e.g., cells, virus and bacteriophage, containing the target molecules from the samples. The conventional separation methods are either time-consuming or include some expansive or complicated procedures such as centrifugation and chromatography. So it is difficulty to realize the automation, micromation and universality of the conventional separation methods.

Because of their paramagnetism, magnetic micro-beads can selectively bind with biomaterials and the motion of magnetic micro-beads-biomaterials conjugates can be controlled by the magnetic field, so they are widely used in the separation of the large biological molecules and cells. However, current separation technique using the magnetic microbeads is based on the antibody derivation, so it is expensive and requires rigorous transportation and preservation conditions. Its use in the biological separation and laboratory operation is limited.

The objective of this invention is to overcome the problems and disadvantages of the conventional separation methods by providing an original method to adsorb nonspecifically or with low specificity and separate the biological materials by use of the paramagnetism, high dispersity, and adhesiveness with karyocytes of the magnetic micro-beads and the precipitation of the chemical agents.

DISCLOSURE OF THE INVENTION

The present invention relates to the separation of target cells, cellular organelles or viruses (such as leukocyte, virus, epithelial cell and cultured cell) containing target biological molecules (such as nucleic acid and protein) from various sources, e.g., whole blood, saliva, serum, marrow, saliva, urine and culture solution of cells and tissues, using nonspecific or low-specificity adsorption and the paramagnetism of the magnetic micro-beads. Under the appropriate buffer, the magnetic micro-beads can be separated from the bio-conjugates. The separated cells can be used in cell culture, drug screening, bio-chemical reactions and biological analysis. This simple and rapid separation method can be used in sample preparation of different scales, especially for small-quantity and microscale samples and it is easy to build up automatic and micromatic device.

In one aspect, the present invention is directed to a process for isolating a target cell, cellular organelle or virus from a sample, which process comprises: a) contacting a sample containing or suspected of containing a target cell, cellular organelle or virus with a magnetic microbead, said magnetic microbead not comprising a moiety that binds to said target cell, cellular organelle or virus with high specificity; b) allowing said target cell, cellular organelle or virus, if present in said sample, to bind to said magnetic microbead nonspecifically or with low specificity to form a conjugate between said target cell, cellular organelle or virus and said magnetic microbead; and c) separating said conjugate from other undesirable constituents via a magnetic force to isolate said target cell, cellular organelle or virus from said sample.

In another aspect, the present invention is directed to a kit for isolating a target cell, cellular organelle or virus from a sample, which kit comprises in a same or different container(s): a) a magnetic microbead for contacting a sample containing or suspected of containing a target cell, cellular organelle or virus, said magnetic microbead not comprising a moiety that binds to said target cell, cellular organelle or virus with high specificity; b) means for allowing said target cell, cellular organelle or virus, if present in said sample, to bind to said magnetic microbead nonspecifically or with low specificity to form a conjugate between said target cell, cellular organelle or virus and said magnetic microbead; and c) means for separating said conjugate from other undesirable constituents via a magnetic force to isolate said target cell, cellular organelle or virus from said sample.

In still another aspect, the present invention is directed to a process for isolating a virus or bacteriophage from a sample, which process comprises: a) removing cells from a sample containing or suspected of containing a target virus or bacteriophage; b) contacting said cell-free sample with a magnetic microbead, said magnetic microbead not comprising a moiety that binds to said target virus or bacteriophage with high specificity; c) allowing said target virus or bacteriophage, if present in said sample, to bind to said magnetic microbead nonspecifically or with low specificity to form a conjugate between said target virus or bacteriophage and said magnetic microbead; and c) separating said conjugate from other undesirable constituents via a magnetic force to isolate said target virus or bacteriophage from said sample.

In yet another aspect, the present invention is directed to a kit for isolating a virus or bacteriophage from a sample, which kit comprises in a same or different container(s): a) means for removing cells from a sample containing or suspected of containing a target virus or bacteriophage; b) a magnetic microbead for contacting said cell-free sample, said magnetic microbead not comprising a moiety that binds to said target cell, cellular organelle or virus with high specificity; c) means for allowing said target virus or bacteriophage, if present in said cell-free sample, to bind to said magnetic microbead nonspecifically or with low specificity to form a conjugate between said target virus or bacteriophage and said magnetic microbead; and d) means for separating said conjugate from other undesirable constituents via a magnetic force to isolate said target virus or bacteriophage from said sample.

BRIEF DESCRIPTION OF THE DRAWINGS

Use magnet to immobilize the bead-target complex to the side of the tube. Remove supernatant. D: Wash and resuspend the isolated target cell.

FIG. 2 illustrates PCR products of the HLA-A allele gene (1,100 bp). The positive control is PCR product from DNA isolated using conventional method. Three (3) μl of sample were applied to the gel. Lanes are (M): DNA mass ladder (DL-2000, TaKaRa, Japan); (1): negative control; (2): positive control; (3, 4): the "Microbead-PCR" product with templates prepared from whole blood sample by our protocol; (5, 6): the "Microbead-PCR" products with templates prepared from saliva sample by our protocol; (7, 8): 2 μl of whole blood added as templates; and (9, 10): 2 μl of saliva added as templates.

MODES OF CARRYING OUT THE INVENTION

Figure 1:
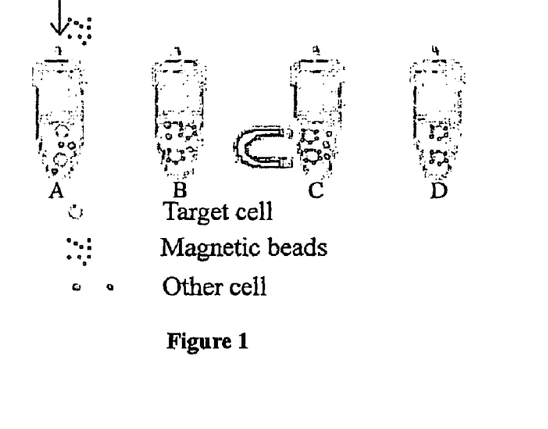
FIG. 1 illustrates an exemplary magnetism based cell separation. A: Add magnetic beads for target cell; B: Incubate suspension to allow magnetic beads to bind to target cell; C.
Figure 2:
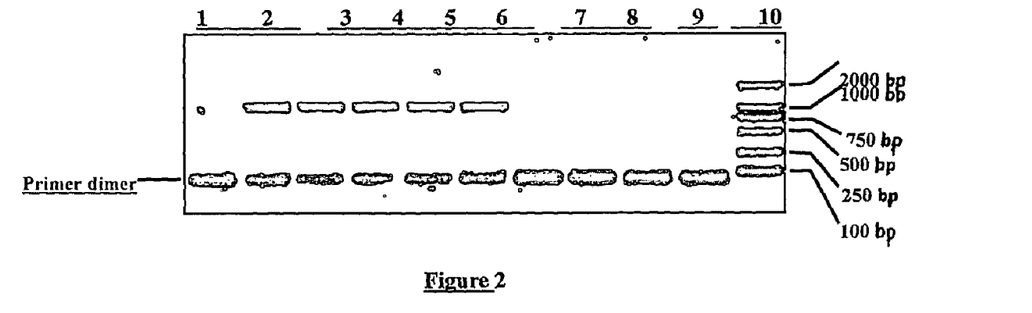

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "specific binding" refers to the binding of one material to another in a manner dependent upon the presence of a particular molecular structure. For example, a receptor will selectively bind ligands that contain the chemical structures complementary to the ligand binding site(s).

As used herein, "specific binding pair" refers to any substance, or class of substances, which has a specific binding affinity for the ligand to the exclusion of other substances. In one embodiment, the specific binding pair includes specific binding assay reagents which interact with the sample ligand or the binding capacity of the sample for the ligand in an immunochemical manner. For example, there will be an antigen-antibody or hapten-antibody relationship between reagents and/or the sample ligand or the binding capacity of the sample for the ligand. Additionally, it is well understood in the art that other binding interactions between the ligand and the binding partner serve as the basis of specific binding assays, including the binding interactions between hormones, vitamins, metabolites, and pharmacological agents, and their respective receptors and binding substances. (See e.g., Langan et al. eds., Ligand Assay, pp. 211 et seq., Masson Publishing U.S.A. Inc., New York, 1981).

As used herein, "said magnetic microbead not comprising a moiety that binds to said target cell, cellular organelle or virus with high specificity" means that there is no specific binding between the magnetic microbead and the target cell, cellular organelle or virus. For example, the binding between the magnetic microbead and the target cell, cellular organelle or virus is not mediated by a specific interaction between complementary biomolecules, such an interaction between ligand and receptor, antigen and antibody, substrate and enzyme, carbohydrate and lectin, and complementary nucleic acids, etc. It also means that the magnetic microbead does not comprise a moiety that can form a specific binding pair with the target cell, cellular organelle or virus. For example, the moiety that is not comprised in the magnetic microbead is a biomolecule such as an amino acid, a peptide, a protein, a nucleoside, a nucleotide, an oligonucleotide, a nucleic acid, a vitamin, a monosaccharide, an oligosaccharide, a carbohydrate, a lipid and a complex thereof. Preferred the moiety that is not comprised in the magnetic microbead is an antibody that specifically binds to the target cell, cellular organelle or virus.

As used herein, "target cell, cellular organelle or virus, if present in said sample, to bind to said magnetic microbead nonspecifically or with low specificity" has the same meaning as "said magnetic microbead not comprising a moiety that binds to said target cell, cellular organelle or virus with high specificity," i.e., there is no specific binding between the magnetic microbead and the target cell, cellular organelle or virus, the binding between the magnetic microbead and the target cell, cellular organelle or virus is not mediated by a specific interaction between complementary biomolecules and the magnetic microbead does not comprise a moiety that can form a specific binding pair with the target cell, cellular organelle or virus.

As used herein, "antibody" refers to specific types of immunoglobulin, i.e., IgA, IgD, IgE, IgG, e.g., $IgG_1$, $IgG_2$, $IgG_3$, and $IgG_4$, and IgM. An antibody can exist in any suitable form and also encompass any suitable fragments or derivatives. Exemplary antibodies include a polyclonal antibody, a monoclonal antibody, a Fab fragment, a Fab' fragment, a $F(ab')_2$ fragment, a Fv fragment, a diabody, a single-chain antibody and a multi-specific antibody formed from antibody fragments.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 micron) with non-compartmentalized circular DNA and ribosomes of about 70 S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein, "sample" refers to anything which may contain a target cell, cellular organelle or virus to be separated or isolated using the present methods and/or kits. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). Biological tissues may be processed to obtain cell suspension samples. The sample may also be a mixture of cells prepared in vitro. The sample may also be a cultured cell suspension. In case of the biological samples, the sample may be crude samples or processed samples that are obtained after various processing or preparation on the original samples. For example, various cell separation methods (e.g., magnetically activated cell sorting) may be applied to separate or enrich target cells from a body fluid sample such as blood. Samples used for the present invention include such target-cell enriched cell preparation.

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

As used herein, "magnetic substance" refers to any substance that has the properties of a magnet, pertaining to a magnet or to magnetism, producing, caused by, or operating by means of, magnetism.

As used herein, "magnetizable substance" refers to any substance that has the property of being interacted with the field of a magnet, and hence, when suspended or placed freely in a magnetic field, of inducing magnetization and producing a magnetic moment. Examples of magnetizable substances include, but are not limited to, paramagnetic, ferromagnetic and ferrimagnetic substances.

As used herein, "paramagnetic substance" refers to the substances where the individual atoms, ions or molecules possess a permanent magnetic dipole moment. In the absence of an external magnetic field, the atomic dipoles point in random directions and there is no resultant magnetization of the substances as a whole in any direction. This random orientation is the result of thermal agitation within the substance. When an external magnetic field is applied, the atomic dipoles tend to orient themselves parallel to the field, since this is the state of lower energy than antiparallel position. This gives a net magnetization parallel to the field and a positive contribution to the susceptibility. Further details on "paramagnetic substance" or "paramagnetism" can be found in various literatures, e.g., at Page 169-page 171, Chapter 6, in "Electricity and Magnetism" by B. I. Bleaney and B. Bleaney, Oxford, 1975.

As used herein, "ferromagnetic substance" refers to the substances that are distinguished by very large (positive) values of susceptibility, and are dependent on the applied magnetic field strength. In addition, ferromagnetic substances may possess a magnetic moment even in the absence of the applied magnetic field, and the retention of magnetization in zero field is known as "remanence". Further details on "ferromagnetic substance" or "ferromagnetism" can be found in various literatures, e.g., at Page 171-page 174, Chapter 6, in "Electricity and Magnetism" by B. I Bleaney and B. Bleaney, Oxford, 1975.

As used herein, "ferrimagnetic substance" refers to the substances that show spontaneous magnetization, remanence, and other properties similar to ordinary ferromagnetic materials, but the spontaneous moment does not correspond to the value expected for full parallel alignment of the (magnetic) dipoles in the substance. Further details on "ferrimagnetic substance" or "ferrimagnetism" can be found in various literatures, e.g., at Page 519-524, Chapter 16, in "Electricity and Magnetism" by B. I. Bleaney and B. Bleaney, Oxford, 1975.

As used herein, "metal oxide particle" refers to any oxide of a metal in a particle form. Certain metal oxide particles have paramagnetic or super-paramagnetic properties. "Paramagnetic particle" is defined as a particle which is susceptible to the application of external magnetic fields, yet is unable to maintain a permanent magnetic domain. In other words, "paramagnetic particle" may also be defined as a particle that is made from or made of "paramagnetic substances". Non-limiting examples of paramagnetic particles include certain metal oxide particles, e.g., $Fe_3O_4$ particles, metal alloy particles, e.g., CoTaZr particles.

As used herein, "poisonous agent" refers to any substance that is harmful to human health, e.g., chloroform or phenol.

As used herein, "the sample, e.g., the whole blood, marrow or lympha is fresh" means that the sample has been obtained or isolated from its natural source within about 12 hours. Preferably, the sample has been obtained or isolated from its natural source within about 10, 5, 4, 3, 2 hours, 1 hour, 30, 20, 10, 5, 2 minutes or 1 minute.

As used herein, "the sample, e.g., the whole blood, marrow or lympha is low-temperature conserved" means that the sample has been conserved at a temperature about at or below 0° C.

As used herein, "highly hydratable compound" refers to any substance, especially an organic compound, that can be easily hydrated.

B. METHODS AND KITS FOR ISOLATING A TARGET CELL, CELLULAR ORGANELLE OR VIRUS

In one aspect, the present invention is directed to a process for isolating a target cell, cellular organelle or virus from a sample, which process comprises: a) contacting a sample containing or suspected of containing a target cell, cellular organelle or virus with a magnetic microbead, said magnetic microbead not comprising a moiety that binds to said target cell, cellular organelle or virus with high specificity; b) allowing said target cell, cellular organelle or virus, if present in said sample, to bind to said magnetic microbead nonspecifically or with low specificity to form a conjugate between said target cell, cellular organelle or virus and said magnetic microbead; and c) separating said conjugate from other undesirable constituents via a magnetic force to isolate said target cell, cellular organelle or virus from said sample.

In another aspect, the present invention is directed to a kit for isolating a target cell, cellular organelle or virus from a sample, which kit comprises in a same or different container(s): a) a magnetic microbead for contacting a sample containing or suspected of containing a target cell, cellular organelle or virus, said magnetic microbead not comprising a moiety that binds to said target cell, cellular organelle or virus with high specificity; b) means for allowing said target cell, cellular organelle or virus, if present in said sample, to bind to said magnetic microbead nonspecifically or with low specificity to form a conjugate between said target cell, cellular organelle or virus and said magnetic microbead; and c) means for separating said conjugate from other undesirable constituents via a magnetic force to isolate said target cell, cellular organelle or virus from said sample. The kit can further comprise an instruction for using the kit for isolating a target cell, cellular organelle or virus from a sample.

The present processes and kits can be used to isolate any suitable target cell, cellular organelle or virus from a sample. Exemplary target cells include animal cells, plant cells, fungus cells, bacterium cells, recombinant cells and cultured cells. Exemplary target cellular organelles include nuclei, mitochondria, chloroplasts, ribosomes, ERs, Golgi apparatuses, lysosomes, proteasomes, secretory vesicles, vacuoles and microsomes. Exemplary target viruses include eucaryotic cell viruses and bacteriophages.

The magnetic microbeads can be prepared by any suitable methods. For example, the methods disclosed in CN 01/109870.8 or WO02/075309 can be used. Any suitable magnetizable substance can be used to prepare the magnetic microbeads useful in the present processes and kits. No-limiting examples of the magnetizable substances include ferrimagnetic substance, ferromagnetic substance, paramagnetic substance or superparamagnetic substances. In a specific embodiment, the magnetic microbeads comprise a paramagnetic substance, e.g., a paramagnetic metal oxide composition. Preferably, the paramagnetic metal oxide composition is a transition metal oxide or an alloy thereof. Any suitable transition metals can be used, such as iron, nickel, copper, cobalt, manganese, tantalum (Ta), zinc and zirconium (Zr). In a preferred embodiment, the metal oxide composition is $Fe_3O_4$ or $Fe_2O_3$. In another example, the magnetizable substance used in the magnetic microbeads comprises a metal composition. Preferably, the metal composition is a transition metal composition or an alloy thereof such as iron, nickel, copper, cobalt, manganese, tantalum, zirconium and cobalt-tantalum-zirconium (CoTaZr) alloy.

The magnetic microbeads may be prepared from the available primary beads, from raw materials or from metal oxides that are encapsulated by monomers which when crosslinked form rigid, polymeric coatings as disclosed in U.S. Pat. No. 5,834,121. As used herein, "rigid" refers to a polymeric coating that is cross linked to the extent that the polymeric coating stabilizes the metal oxide particle within the coating (i.e. the coating essentially does not swell or dissolve) so that the particle remains enclosed therein. As used herein, "microporous" refers to a resinous polymeric matrix that swells or expands in polar organic solvent. As used herein, "load" is used to mean the capacity of the bead for attachment sites useful for functionalization or derivatization.

Suitable substances which may be incorporated as magnetizable materials, for example, include iron oxides such as magnetite, ferrites of manganese, cobalt, and nickel, hematite and various alloys. Magnetite is the preferred metal oxide. Frequently, metal salts are taught to be converted to metal oxides then either coated with a polymer or adsorbed into a bead comprising a thermoplastic polymer resin having reducing groups thereon. When starting with metal oxide particles to obtain a hydrophobic primary bead, it is necessary to provide a rigid coating of a thermoplastic polymer derived from vinyl monomers, preferably a cross-linked polystyrene that is capable of binding or being bound by a microporous matrix. Magnetic particles may be formed by methods known in the art, e.g., procedures shown in Vandenberge et al., *J. of Magnetism and Magnetic Materials*, 15-18:1117-18 (1980); Matijevic, *Acc. Chem. Res.*, 14:22-29 (1981); and U.S. Pat. Nos. 5,091,206; 4,774,265; 4,554,088; and 4,421,660. Examples of primary beads that may be used in this invention are shown in U.S. Pat. Nos. 5,395,688; 5,318,797; 5,283,079; 5,232,7892; 5,091,206; 4,965,007; 4,774,265; 4,654,267; 4,490,436; 4,336,173; and 4,421,660. Or, primary beads may be obtained commercially from available hydrophobic or hydrophilic beads that meet the starting requirements of size, sufficient stability of the polymeric coating to swell in solvents to retain the paramagnetic particle, and ability to adsorb or absorb the vinyl monomer used to form the enmeshing matrix network. Preferably, the primary bead is a hydrophobic, polystyrene encapsulated, paramagnetic bead. Such polystyrene paramagnetic beads are available from Dynal, Inc. (Lake Success, N.Y.), Rhone Poulonc (France), and SINTEF (Trondheim, Norway). The use of toner particles or of magnetic particles having a first coating of an unstable polymer which are further encapsulated to produce an exterior rigid polymeric coating is also contemplated.

The magnetic microbeads used in the present processes and kits can have any suitable size, e.g., having a diameter ranging from about 5 to about 50,000 nanometers.

The magnetic microbeads used in the present processes and kits can be untreated or can be modified, e.g., modified with an organic molecule. In a specific embodiment, the magnetic microbead is modified to comprise a hydroxyl, a carboxyl or an epoxy group.

The present processes can further comprise washing the separated conjugate to remove the undesirable constituents and/or can further comprise recovering the target cell, cellular organelle or virus from the separated conjugate. For example, the target cell, cellular organelle or virus can be released from the separated conjugate with a suitable buffer solution into the buffer and the magnetic microbead is removed from the solution via a magnetic force.

The present processes and kits can be used to isolate any suitable target cell, cellular organelle or virus from any suitable sample. For example, the present processes and kits can be used to isolate any suitable target cell, cellular organelle or virus from a clinical sample. In another example, the present processes and kits can be used to isolate any suitable target cell, cellular organelle or virus from serum, plasma, whole blood, sputum, cerebral spinal fluid, amniotic fluid, urine, gastrointestinal contents, hair, saliva, sweat, gum scrapings, marrow, tissue or cell culture.

The present processes can further comprise recovering a biological material from the isolated target cell, cellular organelle or virus. Exemplary biological materials include amino acids, peptides, proteins, nucleosides, nucleotides, oligonucleotides, nucleic acids, vitamins, monosaccharides, oligosaccharides, carbohydrates, lipids and a complex thereof. Preferably, the biological material to be recovered from the isolated target cell, cellular organelle or virus is an oligonucleotide or a nucleic acid. The present processes can further comprise amplifying the recovered oligonucleotide or nucleic acid. The biological materials can be recovered and/or amplified from the isolated target cell, cellular organelle or virus using any suitable methods (See e.g., Ausabel et al., eds., Current Protocol of Molecular Biology, John Wiley and Sons, Inc (2000)).

The present processes can be performed manually. Preferably, the present processes are automated. Any, some or all steps of the present processes can be automated. For example, the sample contacting, binding, separating, as well as any other additional steps such as washing, target cell, cellular organelle or virus releasing, and biological material recovering or amplifying step(s) can be automated.

The present processes can be performed within any suitable time frame. For example, the present processes can be performed within a time ranging from about 1 minute to about 20 minutes.

The present processes can be performed at any suitable temperature. For example, the present processes can be performed at an ambient temperature ranging from about 0° C. to about 35° C.

The present processes can be performed in an EPPENDORF™ tube. The present processes can be performed in the absence of a precipitation procedure. The present processes can be performed in the absence of a poisonous agent.

In one specific embodiment, the present process is used to isolate a leukocyte from whole blood, marrow or lympha, e.g., fresh or low-temperature conserved whole blood, marrow or lympha. The leukocyte can be contacted with the magnetic microbead in a suitable chemical environment having the following characteristic(s): a) a pH ranging from about 3 to about 7; and/or b) a suitable concentration or amount of an anticoagulant, e.g., acid citrate dextrose (ACD), sodium citrate and sodium heparin, e.g., 23 mM citric acid, 80 mM dextrose and 45 mM sodium citrate.

The process can further comprise washing the separated leukocyte-magnetic-microbead conjugate with a washing buffer to remove the undesirable constituents. Any suitable washing buffer can be used. For example, the washing buffer can be a physiological salt water having a pH at about 6.5 or a phosphate buffer (PBS) having a pH at about 6.5. The leukocyte can be released from the separated leukocyte-magnetic-microbead conjugate with a suitable separation buffer solution into the buffer and the magnetic microbead is removed from the solution via a magnetic force.

In another specific embodiment, the present process is used to isolate a target cell, e.g., an epithelia cast-off cell or a bacteria cell, cellular organelle or virus from saliva, urine and tissue culture. The saliva, urine and tissue culture can be fresh or low-temperature conserved saliva, urine and tissue culture. The target cell, cellular organelle or virus can be contacted with the magnetic microbead in a suitable chemical environment having a pH ranging from about 3 to about 7. The process can further comprise washing the separated conjugate between the target cell, cellular organelle or virus and the magnetic microbead with a washing buffer to remove the undesirable constituents. Any suitable washing buffer can be used. For example, the washing buffer can be a physiological salt water having a pH at about 6.5 or a phosphate buffer (PBS) having a pH at about 6.5. The target cell, cellular organelle or virus can be released from the separated conjugate between the target cell, cellular organelle or virus and the magnetic microbead with a suitable separation buffer solution into the buffer and the magnetic microbead is removed from the solution via a magnetic force. Any suitable separation buffer can be used. For example, the separation buffer can be a Tris-EDTA buffer having a pH ranging from about 6.5 to about 8 and a detergent at a concentration about less than 1% (w/w).

C. PROCESSES AND KITS FOR ISOLATING A VIRUS OR BACTERIOPHAGE

In still another aspect, the present invention is directed to a process for isolating a virus or bacteriophage from a sample, which process comprises: a) removing cells from a sample containing or suspected of containing a target virus or bacteriophage; b) contacting said cell-free sample with a magnetic microbead, said magnetic microbead not comprising a moiety that binds to said target virus or bacteriophage with high specificity; c) allowing said target virus or bacteriophage, if present in said sample, to bind to said magnetic microbead nonspecifically or with low specificity to form a conjugate between said target virus or bacteriophage and said magnetic microbead; and c) separating said conjugate from other undesirable constituents via a magnetic force to isolate said target virus or bacteriophage from said sample.

In yet another aspect, the present invention is directed to a kit for isolating a virus or bacteriophage from a sample, which kit comprises in a same or different container(s): a) means for removing cells from a sample containing or suspected of containing a target virus or bacteriophage; b) a magnetic microbead for contacting said cell-free sample, said magnetic microbead not comprising a moiety that binds to said target cell, cellular organelle or virus with high specificity; c) means for allowing said target virus or bacteriophage, if present in said cell-free sample, to bind to said magnetic microbead nonspecifically or with low specificity to form a conjugate between said target virus or bacteriophage and said magnetic microbead; and d) means for separating said conjugate from other undesirable constituents via a magnetic force to isolate said target virus or bacteriophage from said sample.

The present processes and kits can be used to isolate a virus or bacteriophage from any suitable sample. Exemplary samples include saliva, urine or serum. Preferably, the saliva, urine or serum is fresh or low-temperature conserved saliva, urine or serum.

The present processes and kits can be used to isolating a virus or bacteriophage from any suitable cells. Exemplary cells include epithelia cast-off cells and bacteria cells. The cells can be from the sample by any suitable methods, e.g., centrifugation.

In one specific embodiment, the virus or bacteriophage is contacted with the magnetic microbead in the presence of: a) a highly hydratable compound at a concentration ranging from about 10% (v/v) to about 100% (v/v); and/or b) a salt at a concentration ranging from about 2.5 M to about 5.0 M.

Any suitable highly hydratable compound, e.g., organic compound, can be used in the present processes and kits. Exemplary high-hydrability organic compounds include ethanol, acetone and polyethylene glycol. Any suitable salt can be used in the present processes and kits. Exemplary salt includes sodium chloride.

The process can further comprise washing the separated conjugate between the target virus or bacteriophage and the magnetic microbead with a washing buffer to remove the undesirable constituents. Any suitable washing buffer can be used. For example, the washing buffer can be a physiological salt water having a pH at about 6.5 or a phosphate buffer (PBS) having a pH at about 6.5.

The process can further comprise releasing the target virus or bacteriophage from the separated conjugate between the target virus or bacteriophage and the magnetic microbead with a suitable separation buffer solution into the buffer and the magnetic microbead is removed from the solution via a magnetic force.

The general teachings of the above Section B, e.g., target cells, samples, properties of the magnetic microbeads, washing and separation buffers and procedures, biological materials to be released, various aspects of automation, time, temperature and locations wherein the isolation are conducted, the absence of certain procedure or substance, etc., are also applicable to this Section C.

D. EXEMPLARY EMBODIMENTS

The embodiments described herein relate to the separation of cells and biological materials (such as leukocytes, virus, epithelial cells and cultured cells) containing target biological molecules (such as nucleic acid and protein) from the whole blood, saliva, serum, marrow, saliva, urine and culture solution of cells and tissues using the nonspecific or low-specificity adsorption and the paramagnetism of the magnetic micro-beads. Under the appropriate buffer, the magnetic micro-beads can be separated from the bio-conjugates. The separated cells can be used in cell culture, drug screening, bio-chemical reactions and biological analysis.

An important aspect of these embodiments is to use the paramagnetism, high-dispersity, and adhesiveness with karyocytes of the magnetic micro-beads. They can nonspecifically adsorb the biological materials or with low specificity and drag the biological materials from the samples because of the precipitation of the chemical agents. This simple and rapid separation method can be used in sample preparation of different scales, especially for small-quantity and microscale samples and it is easy to build up automatic and micromatic device.

1. Nonspecific Adsorption and Separation of Leukocytes from the Whole Blood

The conventional separation techniques of leukocytes from the whole blood often include: (1) density gradient centrifugation; (2) breaking the erythrocytes with chemical agents first and then extracting the leukocytes through centrifugation; (3) affinity chromatography of the derivative solid material which is the specific antibody connected with the antigen on the leukocytes surface. But these methods are expensive and difficulty to realize the automation and micromation.

In this embodiment, the magnetic micro-beads coated with organic materials can adsorb the leukocytes nonspecifically and effectively under the appropriate chemical and physical circumstance. So the operation is simple and rapid. Together with the use of the micro-beads PCR program, the whole separation process of the leukocytes from the whole blood costs only a few minutes without centrifugation and temperature rise. So it is easy to build up automatic mini separation device.

1.1. Preparation of the Solid Carrier

The preparation of the coated magnetic micro-beads can be by any suitable methods, e.g., methods disclosed in CN 01/109870.8 or WO02/075309. The preparation method and diameter of the magnetic micro-beads have insignificant influence on the extracted leukocytes. But the magnetic micro-beads modified with hydroxyl, carboxyl and epoxy groups have better separation effect. It is not necessary to treat the magnetic micro-beads with other chemical treatment methods.

1.2 Operation Program (1) Small magnetic micro-beads (suspended in Tris-EDTA buffer, pH 6.0) are added into the whole blood sample. The mixture is agitated gently by vortexing and incubated at room temperature for 3 min.

(2) The magnetic micro-beads-leukocytes conjugates are separated by the magnetic field and the supernatant is discarded.

(3) The magnetic micro-bead-leukocytes conjugates are washed twice with 70% ethanol solution or once with PBS buffer.

(4) Some solution of separation buffer is added into the conjugates and the mixture is incubated at room temperature for 10 min. Then the eluant is collected and the leukocytes can be used for related analysis.

1.3. Chemical Agents Content

Separation buffer: TE (pH 7.0): 10 mM EDTA/25 mM Tris-HCl; Tween 20: 0.1%. Alternative separation buffer: Tris-EDTA (pH 7.0): 10 mM EDTA/25 mM Tris-HCl; Tween 20: 0.1%.

1.4. Main Advantages

This method has some main advantages: (1) simple and rapid operation, which only takes about 1-3 min; (2) requiring only an EPPENDORF™ tube, without precipitation; (3) the obtained products suitable for subsequent biological operations; (4) easy to realize automatic operation; (5) safe operation without using poisonous agents; (6) operation at room temperature; (7) easy preservation of the magnetic micro-beads, which has insignificant influence on the separation effect.

2. Nonspecific Adsorption and Separation of Target Cells from Saliva, Serum, Urine and Cell Culture 2.1. Operation Program (1) Small magnetic micro-beads (suspended in Tris-EDTA buffer, pH 6.0) are added into the biological sample. The mixture is agitated gently by vortexing and incubated at room temperature for 3 min.

(2) The magnetic micro-beads-cells conjugates are separated by the magnetic field and the supernatant is discarded.

(3) The magnetic micro-bead-cells conjugates are washed twice with 70% ethanol solution or with PBS buffer.

(4) Some solution of separation buffer is added into the conjugates and the mixture is incubated at room temperature for 10 min. Then the eluant is collected and the cells can be used for related analysis.

2.2. Chemical Agents Content

Separation buffer: Tris-EDTA (pH 7.0): 10 mM EDTA/25 mM Tris-HCl; Tween 20: 0.1%.

2.3. Main Advantages

This method has some main advantages: (1) simple and rapid operation, which only takes about 20 min; (2) requiring only an EPPENDORF™ tube, without precipitation; (3) the obtained products suitable for subsequent biological operations; (4) easy to realize automatic operation; (5) safe operation without poisonous using agents; (6) operation at room temperature; (7) easy preservation of the magnetic micro-beads, which has insignificant influence on the separation effect.

3. Nonspecific Adsorption Separation of Target Virus and Bacteriophage from Saliva, Serum Urine and Cell Culture 3:1. Operation Program (1) Small magnetic micro-beads (suspended in Tris-EDTA buffer, pH 6.0) and 0.2 volume of the sample of the adsorption buffer are added into the biological sample. The mixture is agitated gently by vortexing and incubated at room temperature for 3 min.

(2) The magnetic micro-beads-cells conjugates are separated by the magnetic field and the supernatant is discarded.

(3) The magnetic micro-bead-cells conjugates are washed twice with 70% ethanol solution or with PBS buffer.

(4) Some solution of separation buffer is added into the conjugates and the mixture is incubated at room temperature for 10 min. Then the eluant is collected and the virus or bacteriophage can be used for related analysis.

3.2. Chemical Agents Content (1) adsorption buffer NaCl 2.5 M, PEG 20% (W/V).

(2) separation buffer TE (pH 7.0): 10 mM EDTA/25 mM Tris-HCl; Tween 20: 0.1%.

3.3. Main Advantages

This method has some main advantages: (1) simple and rapid operation, which only takes about 20 min; (2) requiring only an EPPENDORF™ tube, without precipitation; (3) the obtained products suitable for subsequent biological operations; (4) easy to realize automatic operation; (5) safe operation without using poisonous agents; (6) operation at room temperature; (7) easy preservation of the magnetic micro-beads, which has insignificant influence on the separation effect.

E. EXAMPLES

Example 1

Isolation of Leukocytes from Human Whole Blood Using the Magnetic Micro-Beads

Human whole blood from healthy donors was anticoagulated with ACD. The procedure of isolation of leukocytes is as follows. To a 1.5 mL EPPENDORF™ tube containing 30 μL of 15 μg/μL magnetic micro-beads suspended in Tris-EDTA buffer (pH 6.0) was added 300 μL anticoagulated blood. The mixture was agitated gently by vortexing for IS s and incubated at room temperature for 3 min. Then the micro-beads-leukocytes conjugates were immobilized on a magnetic stand and the supernatant was discarded. The magnetic micro-beads-DNA conjugates were washed twice with 100 μL 70% ethanol solution. If the intact structure of the leukocytes was to be kept, the PBS buffer (pH 7.4) instead of ethanol was used to wash the microbeads. After thoroughly evaporating ethanol under room temperature, 50 μL solution of Tris-EDTA-Tween20 (pH 7.0, 10 mmol.L$^{-1}$ Tris-HCl, 1 mmol.L$^{-1}$ EDTA and Tween 20: 0.1%) were added into the conjugates and it was incubated at room temperature for 10 min, to elute the leukocytes. Then the magnetic micro-beads were separated through a magnetic stand. The eluant was collected and the obtained leukocytes can be used to extract big biological molecules (such as nucleic acid and protein). The whole process takes only 15 min.

The magnetic micro-beads with different diameters, coated through different methods have been used for the separation of leukocytes. The coated magnetic micro-beads are compared with the untreated micro-beads. It is shown that the magnetic micro-beads with the diameter of 200 nm have the best separation effect, with 75% separation efficiency at pH 5.5. Using the magnetic micro-beads among the diameters from 20 to 100 nm, there is little difference in the separation efficiency, which is about 50%. The separation efficiency is about 30% using the micro-beads with the diameter of above 300 nm. After modification, the separation efficiency of the magnetic micro-beads increases 15-30%.

Example 2

Isolation of *E. coli*, From Cell Culture and Extraction of Genomic DNA Using the Magnetic Micro-Beads The samples were cultured *E. coli* without plasmid. The procedure is as follows. To a 1.5 mL EPPENDORF™ tube containing 50 μL of 15 μg/μL magnetic micro-beads suspended in Tris-EDTA buffer (pH 6.0) was added 300 μL cell culture. The mixture was agitated gently by vortexing for 15 s and incubated at room temperature for 3 min. Then the micro-beads-cells conjugates were immobilized on a magnetic stand and the supernatant was discarded. The cells were selectively adsorbed on the surface of the micro-beads.

Three hundred (300) μL cell lysis solution (NaI 11.25 g; Urea 12.0 g; Triton X-100 0.65 ml; TE (pH 8.0) 30 ml: 10 mM EDTA/25 mM Tris-HCl) were added into the mixture and the suspension was mixed uniformly by vortexing and incubated at room temperature for 5 min to lyse the leukocytes. Three hundred (300) μL isopropyl alcohol were added into the mixture and the suspension was mixed uniformly by vortexing, then let stand still for 5 min. The magnetic micro-beads-DNA conjugates were immobilized on a magnetic stand and the supernatant was discarded. The micro-beads-DNA conjugates were washed twice with 70% ethanol solution. After thoroughly evaporating ethanol under room temperature, 100 μL solution of Tris-EDTA (pH 6.0) were added into the conjugates and it was incubated at room temperature for 10 min to elute DNA. Then the magnetic micro-beads were immobilized on a magnetic stand. The eluant was collected and analyzed directly by agarose gel electrophoresis and UV spectroscopy. The yield of DNA is 30 μg/ml. Compared with the disruption cells by using SDS and protease phenol/chloroform method, the micro-bead method extracts genomic DNA with lower yield but equal purity.

Example 3

Isolation of Epithelial Cells From Saliva

Saliva was donated by the healthy donors. The procedure is as follows. To a 1.5 mL EPPENDORF™ tube containing 30 μL of 15 μg/μL magnetic micro-beads suspended in Tris-EDTA buffer (pH 6.0) were added 300 μL cell culture. The mixture was agitated gently by vortexing for 15 s and incubated at room temperature for 3 min. Then the micro-beads-cells conjugates were immobilized on a magnetic stand and the supernatant was discarded. The cells were selectively adsorbed on the surface of the micro-beads.

The magnetic micro-beads-cells conjugates were washed twice with 100 μL 70% ethanol solution. If the intact structure of the epithelial cells was to be kept, the PBS buffer (pH 7.4) instead of ethanol was used to wash the micro-beads. After thoroughly evaporating ethanol under room temperature, 50 μL solution of Tris-EDTA-Tween20 (pH 7.0, 10 mmol.L$^{-1}$Tris-HCl, 1 mmol.L$^{-1}$ EDTA and Tween 20: 0.1%) were added into the conjugates and it was incubated at room temperature for 10 min to elute the epithelial cells. Then the magnetic micro-beads were separated through a magnetic stand. The eluant was collected and the obtained epithelial cells can be used to extract big biological molecules (such as nucleic acid and protein). The whole process takes only 15 min. The separation efficiency equals to 60% of that by the centrifugation method.

This is a rapid and effective method for separating epithelial cells from the saliva, which is safe without using poisonous agents. The method produces an eluant containing the epithelial cell and magnetic beads-epithelial cell conjugate, which can used as the template directly in a PCR reaction system for the amplification of the HLA gene. The amplification product is analyzed by agarose gel electrophoresis. The experiment builds-up a rapid and effective microsphere based PCR method for the amplification of the HLA gene. It is quicker and simpler than the traditional method. The template preparation only needs about 10 min, eliminates the use of a PCR inhibiting agent, and has no non-specific amplification.

Example 4

Isolation of Bacteriophage From Cell Culture

The procedure is as follows. Three hundred (300) μL broth bouillon 2xTY containing M13 bacteriophage is centrifuged for 5 min. The supernatant is added into a 1.5 mL EPPENDORF™ tube containing 30 μL of 15 μg/μL magnetic micro-beads with the diameter of 200 nm suspended in Tris-EDTA buffer (pH 6.0). Then 20% polyethylene glycol (NaCl: 2.5M) with 0.2 volume of the mixture is added into the mixture. The mixture is agitated gently by vortexing for 15 s and incubated at room temperature for 3 min. Then the micro-beads-bacteriophage conjugates are immobilized on a magnetic stand and the supernatant is discarded.

The magnetic micro-beads-cells conjugates are washed twice with 100 μL 70% ethanol solution. If the intact structure of the bacteriophage is to be kept, the PBS buffer (pH 7.4) instead of ethanol is used to wash the micro-beads. After thoroughly evaporating ethanol under room temperature, 50 μL solution of Tris-EDTA-Tween20 (pH 7.0, 10 mmol.L$^{-1}$Tris-HCl, 1 mmol.L$^{-1}$ EDTA and Tween 20: 0.1%) is added into the conjugates and it is incubated at room temperature for 10 min to elute the bacteriophage. Then the magnetic micro-beads are separated through a magnetic stand. The eluant is collected and the obtained bacteriophage can be used to extract big biological molecules (such as nucleic acid and protein). The whole process takes only 15 min. The separation efficiency equals to 70% of that by the centrifugation method.

Example 5

Isolation of Influenza Virus From Serum

The procedure is as follows. Three hundred (300) μL serum is mixed with *bacillus* influenza. The mixture is added into a 1.5 mL EPPENDORF™ tube containing 30 μL of 15 μg/μL magnetic micro-beads with the diameter of 200 nm suspended in Tris-EDTA buffer (pH 6.0). Then 20% polyethylene glycol (NaCl: 2.5M) with 0.2 volume of the mixture is added. The mixture is agitated gently by vortexing for 15 s and incubated at room temperature for 3 min. Then the micro-beads-virus conjugates are immobilized on a magnetic stand and the supernatant is discarded.

The magnetic micro-beads-cells conjugates are washed twice with 100 μL 70% ethanol solution. If the intact structure of the virus is to be kept, the PBS buffer (pH 7.4) instead of ethanol is used to wash the micro-beads. After thoroughly evaporating ethanol under room temperature, 50 μL solution of Tris-EDTA-Tween20 (pH 7.0, 10 mmol.L$^{-1}$Tris-HCl, 1 mmol.L$^{-1}$ EDTA and Tween 20: 0.1%) is added into the conjugates and it is incubated at room temperature for 10 min to elute the virus. Then the magnetic micro-beads are separated through a magnetic stand. The eluant is collected and the obtained virus can be used to extract big biological molecules (such as nucleic acid and protein). The whole process takes only 15 min. The separation efficiency equals to 50% of that by the centrifugation method.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A process for isolating a target cell, cellular organelle or virus from a sample, which process comprises:
    a) contacting a sample containing or suspected of containing a target cell, cellular organelle or virus with a magnetic bead, said magnetic bead not comprising a moiety that can form a specific binding pair with said target cell, cellular organelle or virus;
    b) allowing said target cell, cellular organelle or virus, if present in said sample, to bind to said magnetic bead nonspecifically to form a conjugate between said target cell, cellular organelle or virus and said magnetic bead; and
    c) separating said conjugate from unbound constituents via a magnetic force to isolate said target cell, cellular organelle or virus from said sample,
    wherein the magnetic bead has a diameter of 200 nm and is modified to comprise a hydroxyl, a carboxyl or an epoxy group.

2. The process of claim 1, wherein the target cell is selected from the group consisting of an animal cell, a plant cell, a fungus cell, a bacterium cell, a recombinant cell and a cultured cell.

3. The process of claim 1, wherein the target cellular organelle is selected from the group consisting of a nuclei, a mitochondrion, a chloroplast, a ribosome, an ER, a Golgi apparatus, a lysosome, a proteasome, a secretory vesicle, a vacuole and a microsome.

4. The process of claim 1, wherein the target virus is an eucaryotic cell virus or a bacteriophage.

5. The process of claim 1, which further comprises washing the separated conjugate to remove the unbound constituents.

6. The process of claim 1, which further comprises recovering the target cell, cellular organelle or virus from the separated conjugate.

7. The process of claim 6, wherein the target cell, cellular organelle or virus are released from the separated conjugate with a suitable buffer solution into the buffer and the magnetic bead is removed from the solution via a magnetic force.

8. The process of claim 1, wherein the sample is a clinical sample.

9. The process of claim 1, wherein the sample is selected from the group consisting of serum, plasma, whole blood, sputum, cerebral spinal fluid, amniotic fluid, urine, gastrointestinal contents, hair, saliva, sweat, gum scrapings, marrow, tissue and cell culture.

10. The process of claim 1, which further comprises recovering a biological material from the isolated target cell, cellular organelle or virus.

11. The process of claim 10, wherein the biological material is selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

12. The process of claim 11, which further comprises amplifying the recovered oligonucleotide or nucleic acid.

13. The process of claim 1, which is automated.

14. The process of claim 1, which is completed within a time ranging from about 1 minute to about 20 minutes.

15. The process of claim 1, which is conducted in a microcentrifuge tube.

16. The process of claim 1, which is conducted in the absence of a precipitation procedure.

17. The process of claim 1, which is conducted in the absence of a poisonous agent.

18. The process of claim 1, which is conducted at an ambient temperature ranging from about 0° C. to about 35° C.

19. The process of claim 1, which is used to isolate a leukocyte from whole blood, marrow or lymph.

20. The process of claim 19, wherein the whole blood, marrow or lympha lymph is fresh or low-temperature conserved whole blood, marrow or lympha lymph.

21. The process of claim 19, wherein the leukocyte is contacted with the magnetic bead in a suitable chemical environment having the following characteristic(s):
  a) a pH ranging from about 3 to about 7;
  b) an ion concentration that is about larger than one third of that in the normal whole blood; and/or
  c) a suitable concentration of an anticoagulant.

22. The process of claim 21, wherein the anticoagulant is selected from the group consisting of acid citrate dextrose (ACD), sodium citrate and sodium heparin.

23. The process of claim 19, which further comprises washing the separated leukocyte-magnetic bead conjugate with a washing buffer to remove the unbound constituents.

24. The process of claim 23, wherein the washing buffer is a phosphate buffer (PBS) having a pH at about 6.5.

25. The process of claim 19, wherein the leukocyte is released from the separated leukocyte-magnetic bead conjugate with a suitable separation buffer solution into the buffer and the magnetic bead is removed from the solution via a magnetic force.

26. The process of claim 1, which is used to isolate a target cell, cellular organelle or virus from saliva, urine and tissue culture.

27. The process of claim 26, wherein the target cell is an epithelia cast-off cell or a bacteria cell.

28. The process of claim 26, wherein the saliva, urine and tissue culture is fresh or low-temperature conserved saliva, urine and tissue culture.

29. The process of claim 26, wherein the target cell, cellular organelle or virus is contacted with the magnetic microbead in a suitable chemical environment having a pH ranging from about 3 to about 7.

30. The process of claim 26, which further comprises washing the separated conjugate between the target cell, cellular organelle or virus and the magnetic microbead with a washing buffer to remove the undesirable constituents.

31. The process of claim 30, wherein the washing buffer is physiological salt water having a pH at about 6.5 or a phosphate buffer (PBS) having a pH at about 6.5.

32. The process of claim 26, wherein the target cell, cellular organelle or virus is released from the separated conjugate between the target cell, cellular organelle or virus and the magnetic microbead with a suitable separation buffer solution into the buffer and the magnetic microbead is removed from the solution via a magnetic force.

33. The process of claim 32, wherein the separation buffer is a Tris-EDTA buffer having a pH ranging from about 6.5 to about 8 and a detergent at a concentration about less than 1% (w/w).

34. The process of claim 23, wherein the washing buffer has a pH of about 6.5.

35. The process of claim 1, wherein the magnetic microbead comprises a magnetizable substance selected from the group consisting of a paramagnetic substance, a ferromagnetic substance and a ferrimagnetic substance.

36. The process of claim 35, wherein the magnetizable substance comprises a metal composition.

37. The process of claim 36, wherein the metal composition is a transition metal composition or an alloy thereof.

38. The process of claim 35, wherein the transition metal is selected from the group consisting of iron, nickel, copper, cobalt, manganese, tantalum, zirconium and cobalt-tantalum-zirconium (CoTaZr) alloy.

* * * * *